United States Patent [19]
Scott et al.

[11] Patent Number: 5,201,738
[45] Date of Patent: Apr. 13, 1993

[54] BIODEGRADABLE BIOCOMPATIBLE ANTI-DISPLACEMENT DEVICE FOR PROSTHETIC BONE JOINTS

[75] Inventors: Richard D. Scott, Dedham, Mass.; Deger C. Tunc, East Brunswick, N.J.

[73] Assignee: Johnson & Johnson Orthopaedics, Inc., Raynham, Mass.

[21] Appl. No.: 624,829

[22] Filed: Dec. 10, 1990

[51] Int. Cl.$^5$ .................................................. A61F 2/30
[52] U.S. Cl. .......................................... 606/77; 606/72; 623/18
[58] Field of Search ............... 606/72, 76, 77, 53, 606/60, 73, 86, 89; 623/27, 16, 18

[56] References Cited

U.S. PATENT DOCUMENTS

| | | |
|---|---|---|
| 3,528,109 | 9/1970 | Scales . |
| 3,636,956 | 1/1972 | Schneider . |
| 3,641,590 | 2/1972 | Michele ................................. 623/22 |
| 3,903,549 | 9/1975 | Deyerle ................................. 623/22 |
| 4,052,988 | 11/1977 | Doddi . |
| 4,280,954 | 7/1981 | Yannas et al. . |
| 4,356,572 | 11/1982 | Guillemin et al. . |
| 4,550,449 | 11/1985 | Tunc . |
| 4,563,778 | 1/1986 | Roche et al. . |
| 4,792,337 | 12/1988 | Muller ................................. 623/22 |
| 4,828,565 | 5/1989 | Duthoit et al. . |
| 4,840,632 | 6/1989 | Kampner ............................... 623/22 |
| 4,851,006 | 7/1989 | Tuke . |
| 4,919,674 | 4/1990 | Schelhas ............................... 623/22 |
| 4,936,861 | 6/1990 | Muller et al. ........................ 623/22 |
| 4,955,325 | 9/1990 | Zarnowski et al. .................. 623/22 |
| 4,990,161 | 2/1991 | Kampner ........................... 623/22 X |

OTHER PUBLICATIONS

Tunc et al., Advances in Biomedical Polymers, Plenum Press, (1987).

Primary Examiner—Robert A. Hafer
Assistant Examiner—Sam Rimell
Attorney, Agent, or Firm—Hamilton, Brook, Smith & Reynolds

[57] ABSTRACT

An anti-displacement device and method are disclosed for implantation of a prosthetic bone joint in a bone. A biodegradable biocompatable anti-displacement device comprising a biodegradable biocompatible polymer is directed through an orifice, defined by a cup of a prosthetic bone joint, and into interfering contact with bone tissue of the bone. Displacement of the cup is thereby sufficiently limited to allow bone tissue growth at the cup to fix the prosthetic bone joint to the bone while body fluid at the bone tissue and contacting the elongate member biodegrades the elongate member.

16 Claims, 6 Drawing Sheets

BIODEGRADABLE BIOCOMPATIBLE ANTI-DISPLACEMENT DEVICE FOR PROSTHETIC BONE JOINTS

BACKGROUND OF THE INVENTION

Prosthetic bone joints have applications as replacements for mammalian joints afflicted by disease, such as arthritis, and by injury. Growth of bone tissue is often employed to permanently fix implanted prosthetic bone joints. However, displacement of prosthetic bone joints typically must be limited for an initial period following implantation to allow sufficient bone tissue growth to permanently fix the prosthetic bone joints.

Metallic screws and spikes have been used to limit displacement of prosthetic bone joints during the initial period of bone tissue growth required for permanent fixation. These metallic screws and spikes however, generally are not removed after fixation of prosthetic bone joints is complete. Compressive stress imparted by prosthetic bone joints to bones ultimately can deform the bones and cause metallic screws and spikes to fracture. Micromotion between the screws and prosthetic device can cause fretting with release of potentially toxic metal debris into the surrounding tissue. Rupture of blood vessels within bones and severe injury to bones can result from such fracture.

A need exists therefore, for a new device and method of implanting prosthetic bone joints which overcome or minimize the aforementioned problems.

SUMMARY OF THE INVENTION

The present invention relates to a new device and method for sufficiently limiting displacement of a cup of an implanted prosthetic bone joint to allow bone tissue growth at the cup to fix the prosthetic bone joint to the bone.

A device for sufficiently limiting displacement of a cup of an implanted prosthetic bone joint to allow bone tissue growth at the cup to fix the prosthetic bone joint to the bone comprises an elongate member comprising a biodegradable biocompatible polymer. The elongate member extends from the cup into interfering contact with cancellous bone tissue of the bone, whereby displacement of the cup of the prosthetic bone joint is sufficiently limited and whereby the elongate member is biodegraded by body fluid at the bone tissue contacting the elongate member.

In a method for fixing a prosthetic bone joint to a bone, the improvement comprises directing an elongate member comprising a biodegradable biocompatible polymer through an orifice defined by a cup of the prosthetic bone joint and into interfering contact with cancellous bone tissue of the bone Displacement of the cup is sufficiently limited by the elongate member to allow bone tissue growth at the cup to fix the prosthetic bone joint to the bone. The elongate member is biodegraded by body fluid at the bone tissue contacting the elongate member.

The biodegradable biocompatible fixation device of the present invention has many advantages. In general, the biodegradable biocompatible anti-displacement device is biodegraded by body fluid, such as blood, and therefore does not inhibit structural changes in the bone caused by the implanted prosthetic bone joint or by aging of the bone. The biodegradable biocompatible anti-displacement device thus allows fixation of the prosthetic bone joint without presenting a risk that metallic components will fracture and injure surrounding blood vessels and bone tissue. Micromotion between the screws and prosthetic device can cause fretting with release of potentially toxic metal debris into the surrounding tissue.

DETAILED DESCRIPTION OF THE DRAWINGS

DETAILED DESCRIPTION OF THE INVENTION

The features and other details of the device and method of the invention will now be more particularly described with reference to the accompanying drawings and pointed out in the claims. It will be understood that the particular embodiments of the invention are shown by way of illustration and not as limitations of the invention. The principal features of this invention can be employed in various embodiments without departing from the scope of the invention.

Figure 1:
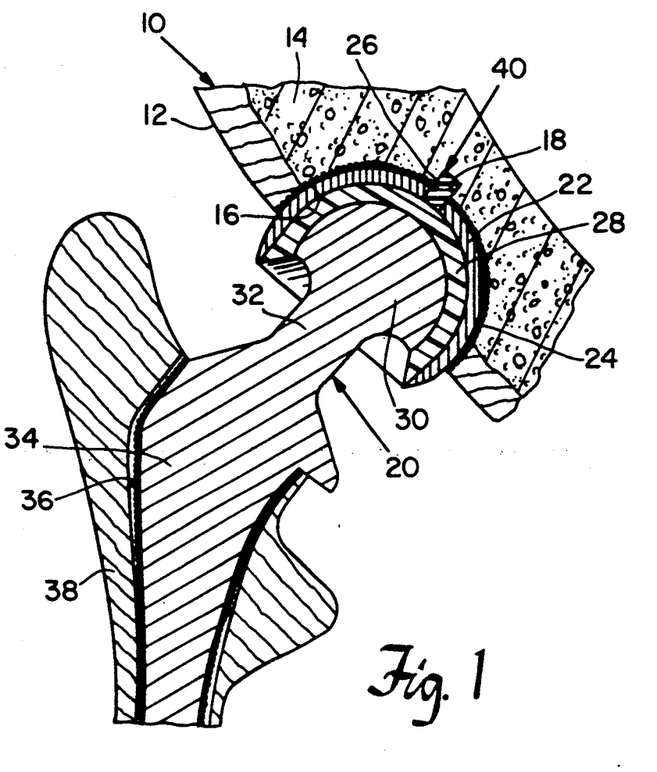
FIG. 1 is a section view of first bone within which a cup of a prosthetic bone joint is implanted and of a second bone within which a stem of the prosthetic bone joint is implanted. The prosthetic bone joint extends between the first bone and the second bone. A section view of one embodiment of the biodegradable biocompatible anti-displacement device of the present invention is also shown wherein the biodegradable biocompatible anti-displacement device extends from the cup of the prosthetic bone joint and into interfering contact with the first bone, thereby limiting displacement of the prosthetic bone joint.

In one embodiment of the present invention, shown in FIG. 1, a first bone 10 includes exterior cortical bone tissue 12 and interior bone tissue 14. Recessed portion 16 of first bone 10 extends within cortical bone tissue 12 and bone tissue 14. Bone tissue 14 defines bore 18. Prosthetic bone joint 20 is implanted in recessed portion 16. Cup 22 of prosthetic bone joint 20 includes surface portion 24 and defines orifice 26. Surface portion 24 is suitable for fixation of prosthetic bone joint 20 to first bone 10 by bone tissue growth at surface portion 24. Liner 28 is disposed within cup 22 for receiving femoral head 30 of prosthetic bone joint 20. Femoral head 30 of prosthetic bone joint 20 is rotatable within liner 28 for movement of prosthetic joint 20. Neck 32 of prosthetic bone joint 20 extends from femoral head 30. Stem 34 of prosthetic bone joint 20 extends from neck 32. Stem 34 is disposed in medullary canal 36 of second bone 38.

The biodegradable biocompatible anti-displacement device of the present invention comprises an elongate member 40. Elongate member 40 extends through orifice 26 of cup 22 and into bore 18 of bone tissue 14. Elongate member 40 is dimensioned and configured relative to orifice 26 and bore 18 to sufficiently limit displacement of cup 22 to allow bone tissue growth at surface portion 24 to fix prosthetic bone joint 20 to first bone 10.

"Displacement," as that term is used herein, means movement of cup 22 relative to bone tissue 14. Displacement of cup 22 is sufficiently limited when, from the time of implantation of elongate member 40 into bone tissue 14, sufficient bone tissue growth at surface portion 24 of cup 22 is allowed to thereby fix cup 22 to first bone 10. Prosthetic bone joint 20 is thereby fixed to first bone 10. "Bone tissue growth," as that term is used herein, can include, for example growth of fibrous tissue and bone formation. In one embodiment, displacement is sufficiently limited when displacement of elongate member 40 is less than one hundred and fifty microns over a period of time greater than about twelve weeks following implantation elongate member 40 into bore 18.

Elongate member 40 comprises a biodegradable biocompatible polymer. "Biodegradable," as that term is used herein, means polymers which are shear resistant and are degraded by a physical or chemical process at constant volume in response to contact with body fluid while implanted in first bone 10. Examples of biodegradation processes include hydrolysis, enzymatic action, oxidation, reduction, emulsion or micelle formulation, solubilization and ion exchange. Suitable conditions for hydrolysis, for example, include exposure of the biodegradable polymer to water at a temperature and a pH of blood circulating through bone tissue 14. The biodegradable polymers are biodegraded and thereupon dissipated by body fluid.

"Shear resistant," as that term is used herein, means that the biodegradable polymer has a sufficient shear resistance to cause elongate member 40 to sufficiently limit displacement of cup 22 to allow permanent fixation of prosthetic bone joint 20 by bone tissue 14 growth at surface portion 24. In one embodiment, shear resistance of elongate member 40, while in contact with bone tissue 14, is greater than about fifteen mpa (megapascals) over a period of time greater than about twelve weeks.

"Constant volume," as that term is used herein, means that, during contact with bone tissue, the biodegradable polymer biodegrades at a rate such that the volume of elongate member 40 diminishes at a rate which sufficiently limits displacement of cup 22. The volume of elongate member 40 can diminish, for example, by increasing porosity of elongate member 40 resulting from contact with body fluid. Alternatively, elongate member 40 can diminish in volume by bioerosion, wherein the volume of elongate member 40 is lost from outward surfaces of elongate member 10 by contact with body fluid. In one embodiment, the rate of biodegradation of the biodegradable polymer is less than about three percent of the initial volume of elongate member 40 over a period of time greater than about twelve weeks.

"Biocompatible," as that term is used herein, means that elongate member 10 exhibits essentially no cytotoxicity while implanted in bone 12.

In one embodiment of the present invention, the biodegradable polymer comprises poly(L(−)lactide), disclosed in U.S. Pat. No. 4,550,449, the teachings of which are incorporated herein by reference. It is to be understood, however, that, in the alternative, poly(D(+)lactide) can be employed. Another biodegradable polymer suitable for use with the present invention is poly-dioxanone, disclosed in U.S. Pat. No. 4,052,988, the teachings of which are incorporated herein by reference.

The general formula for poly(L(−)lactide) is depicted below:

where "n" is the number of repeating L(-)lactide units.

Poly(L(−)lactide) degrades in response to contact with body fluid by hydrolysis. An equation for hydrolysis of poly(L(−)lactide) is:

where "n" represents the number of repeating lactide units contained in the polymer.

Suitable poly(L(−)lactide) can be formed by combining L(-)lactide monomer with a suitable catalyst and exposing the monomer and catalyst to sufficient conditions to substantially polymerize the L(-)lactide monomer. Suitable catalysts for polymerization of the L(-)lactide monomer include, for example, antimony trifluoride, powdered zinc and dibutyl tin oxide. In a preferred embodiment, the catalyst comprises stannous oxalate.

The L(-)lactide monomer can be the only monomer employed to form the poly(L(−)lactide). However, it is to be understood that the L(-)lactide monomer can be polymerized with a suitable comonomer, present in an amount of less than about 10% by weight of the total monomer polymerized. Examples of suitable comonomers include monomers which, when polymerized with the L(-)lactide monomer, form a suitable polymer for forming a biodegradable biocompatible anti-displacement device which sufficiently limits displacement between cup 22 and bone tissue 14. Specific examples of suitable comonomers include: $\beta$-propiolactide; tetramethylglycolide; $\beta$-butyrolactone; $\gamma$-butyrolactone; pivalolactone; $\alpha$-hydroxyacetic acid; $\alpha$-hydroxybutyric acid; $\alpha$-hydroxyisobutyric acid; $\alpha$-hydroxyvaleric acid; $\alpha$-hydroxyisovaleric acid; $\alpha$-hydroxycaproic acid; $\alpha$-hydroxyisocaproic acid; $\alpha$-hydroxy-$\alpha$-ethylbutyric acid; $\alpha$-hydroxy-$\beta$-methylvaleric acid; $\alpha$-hydroxyheptanoic acid; $\alpha$-hydroxyoctanoic acid; $\alpha$-hydroxydecanoic acid; $\alpha$-hydroxymyristic acid; and $\alpha$-hydroxystearic acid.

Sufficient reaction conditions for polymerization of the L(-)lactide monomer in the presence of the catalyst include heating the monomer in the presence of the catalyst to a sufficient temperature and maintaining the L(-)lactide monomer and catalyst at that temperature for a sufficient period of time to cause polymerization of the L(-)lactide monomer and thereby form suitable poly(L(−)lactide). In one embodiment, suitable poly(L(−)lactide) comprises poly(L(−)lactide) having a high enantiomeric purity, high molecular weight and a low content of unreacted monomer.

"High enantiomeric purity," as that term is used herein, means sufficient enantiomeric purity to cause the poly(L(−)lactide) to have a minimun optical rotation of −288° as a one percent volume/volume solution of L(-)lactide in benzene.

Figure 2:
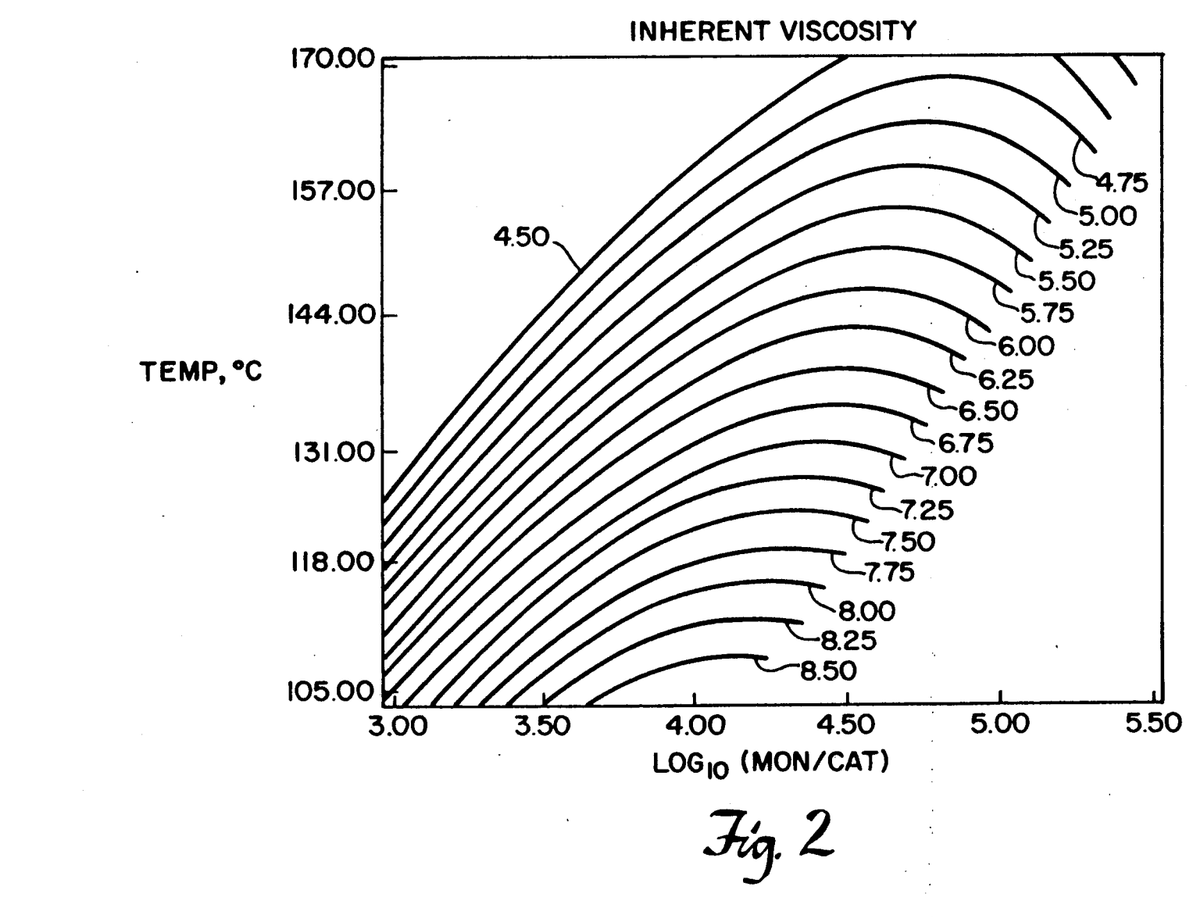
FIG. 2 is a plot of inherent viscosities of poly(L(—)lactides) which are formed under various combinations of monomer-to-catalyst ratio and reaction temperature and which are suitable for forming the biodegradable biocompatible anti-displacement device of the present invention.

"High molecular weight," as that term is used herein, means a molecular weight which will cause the polymer to have an inherent viscosity which is above about 4.5, as determined by forming a one percent solution in chloroform at 25° C. using a Cannon-Fenke Viscometer No. 50. FIG. 2 is a plot of suitable combinations of reaction temperature and monomer-to-catalyst ratio at constant suitable values of inherent viscosity. The inherent viscosities illustrated in FIG. 2 can be defined by the following equation:

Inherent Viscosity $=4.45+9.18L$
$-0.207T-1.51L^2+0.032LT$ where "L" is the $\log_{10}$ of the monomer-to-catalyst ratio and "T" is the temperature of the reaction in degrees celsius.

Figure 3:
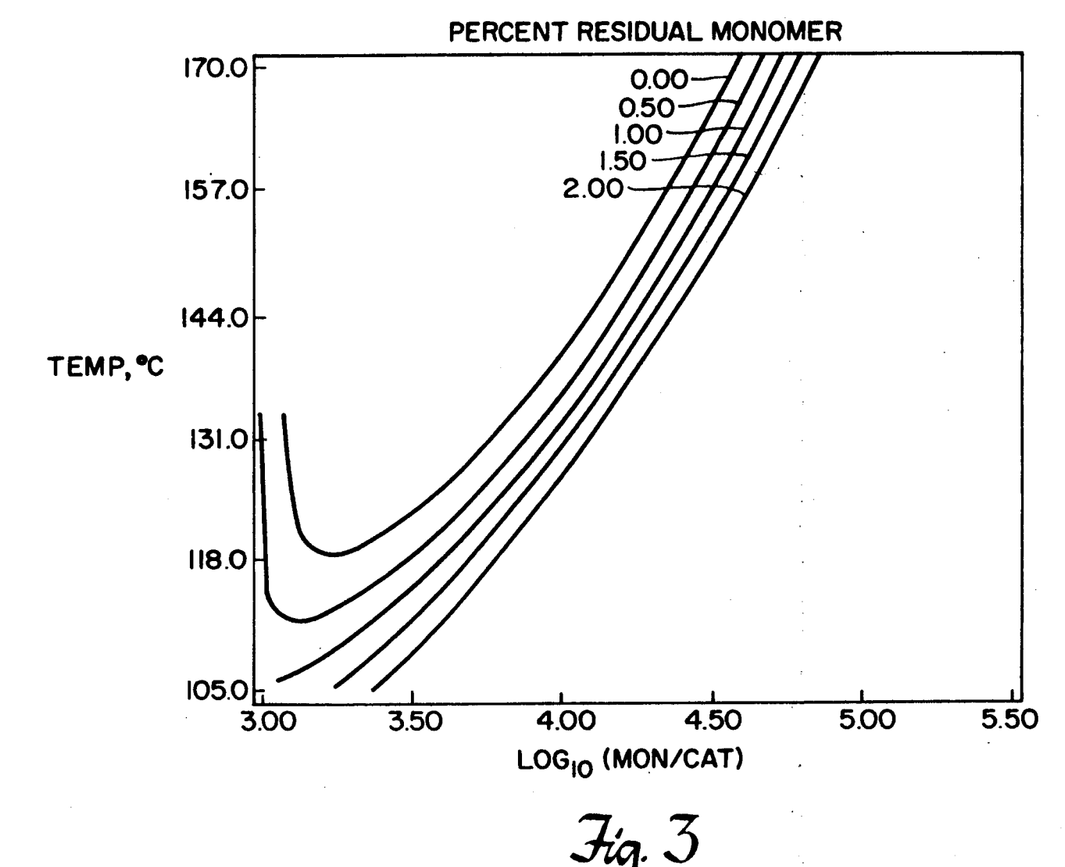
FIG. 3 is a plot of residual monomer content of poly(L(—)lactides) which are formed under various combinations of monomer-to-catalyst ratio and reaction temperature and which are suitable for forming the biodegradable biocompatible anti-displacement device of the present invention.

"Low unreacted monomer content," as that term is used herein, means a residual monomer content in the poly(L(−)lactide) of less than about two percent by weight of the polymer. FIG. 3 is a plot of combinations of suitable reaction temperature and monomer-to-catalyst ratio of the reaction mixture at constant suitable values of residual monomer content. The percent unreacted monomer illustrated in FIG. 3 can be defined by the equation:

Unreacted Monomer $=28.89-15.33L+6.29L^2$
$+0.0026T^2-0.213LT$ where "L" is the $\log_{10}$ monomer-to-catalyst ratio and "T" is the temperature of reaction in degrees celsius.

Figure 4:
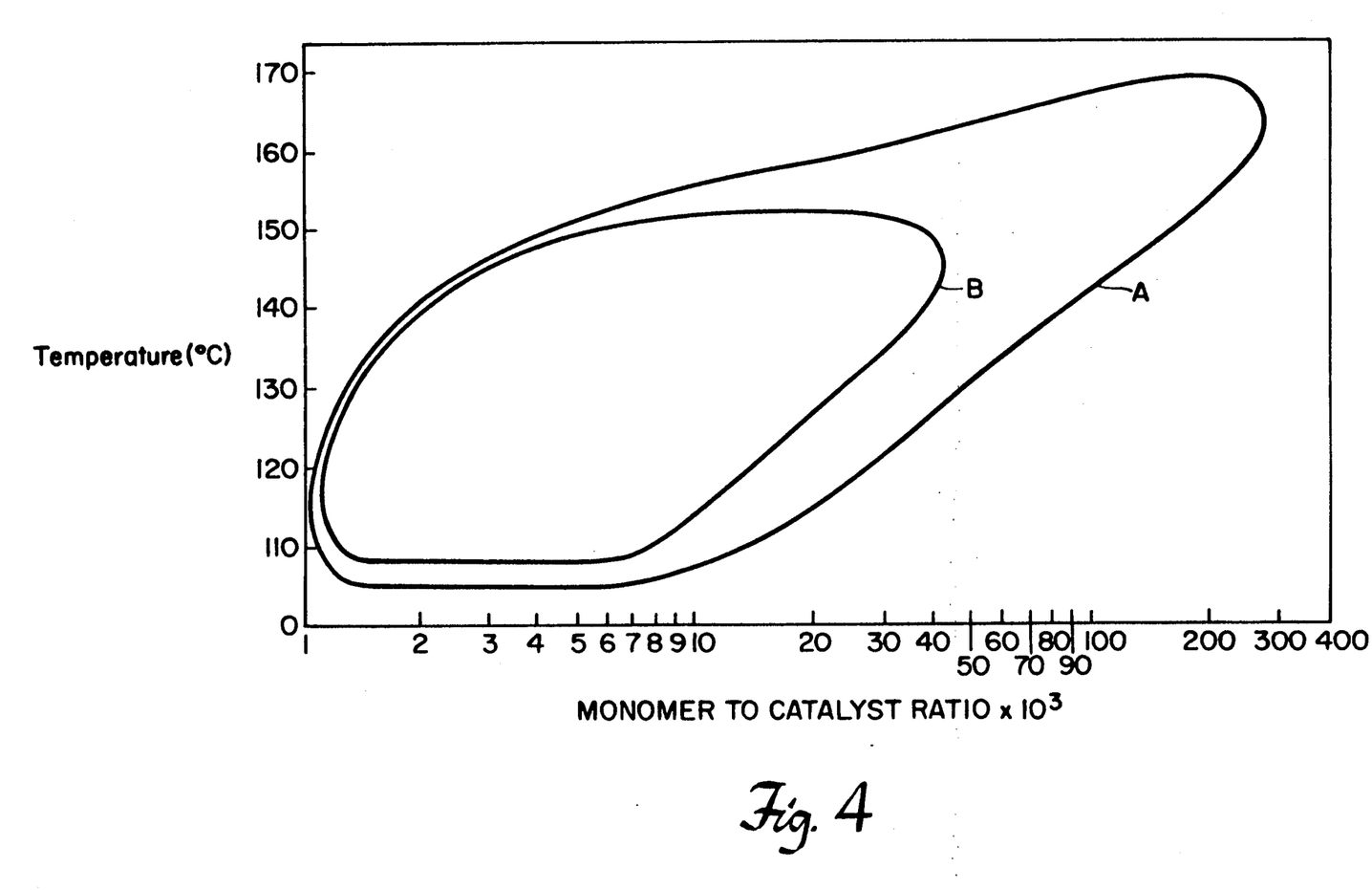
FIG. 4 is a semi-log plot of combinations of monomer-to-catalyst ratio and reaction temperature which can form poly(L(.)lactides) which are suitable for forming the biodegradable biocompatible anti-displacement device of the present invention.

Sufficient reaction conditions for polymerization of the L(-)lactide monomer are illustrated in FIG. 4, which is a semi-log plot of suitable reaction temperatures in degrees celsius relative to various monomer-to-catalyst ratios of the reaction mixture. The area of the plot enclosed within curves A and B are those combinations of reaction temperature and monomer-to-catalyst ratio which will form suitable poly(L(−)lactide). The curve A represents a monomer-to-catalyst ratio in the range of between about 1,050 and about 300,000 and a reaction temperature in the range of between about 105° C. and about 170° C. The area enclosed within curve B are preferred combinations of temperature and monomer-to-catalyst ratio for forming suitable poly(L(−)lactide). The monomer-to-catalyst ratios defining the area within curve B are in the range of between about 1,100 and about 45,000. Reaction temperatures defining curve B are in a range of between about 108° C. and about 155° C. In a particularly preferred embodiment, the monomer-to-catalyst ratio is in the range of between about 1,300 and 20,000 and the reaction temperature is in the range of between about 110° C. and about 130° C.

The L(-)lactide monomer and catalyst are combined in a suitable reaction vessel to form a reaction mixture during exposure to an atmosphere containing nitrogen. A suitable reaction vessel can include, for example, a vacuum flask constructed of glass. The reaction vessel, containing the reaction mixture, is then evacuated by applicaton of vacuum over a period of time of about fifteen minutes to an absolute pressure of about 0.02 mm of mercury and then refilled with dry nitrogen, containing less than about twenty parts per million of moisture. Vacuum evacuation of the reaction vessel is repeated twice. During the third evacuation, the reaction mixture is heated to a suitable reaction temperature. The reaction mixture can be heated by a suitable method, such as by immersing the reaction vessel in a controlled-temperature oil bath while the reaction mixture is magnetically stirred. The reaction mixture is thereby exposed to the reaction temperature for a period of time sufficient to cause a polymerization reaction to form suitable poly(L(−)lactide).

As the polymerization reaction proceeds, the viscosity of the reaction product increases and magnetic stirring is terminated when the magnetic stirrer can no longer be turned. The polymerization reaction is continued until the reaction mixture comprises suitable poly(L(−)lactide). In one embodiment, the period of the polymerization reaction at reaction temperature is in the range of between about fifty hours and about one hundred and twenty hours. Following the reaction period, the poly(L(−)lactide) is cooled and removed from the reaction vessel.

The biodegradable biocompatible anti-displacement device of the present invention can be formed by machining the poly(L(−)lactide) by a suitable method. Alternatively, the poly(L(−)lactide) can be ground into particles suitable for injection molding. The ground particles are then extruded by a suitable method. The extruded polymer is directed from a suitable extrusion means into a suitable mold. The biodegradable biocompatible anti displacement device is then removed from the mold and sterilized.

It is to be understood that the biodegradable biocompatible anti-displacement device can be configured as a peg, pin, spike, screw or other configuration of an elongate member suitable for extending from a prosthetic bone joint into bone tissue. It is to be understood, however, that more than one biodegradable biocompatible anti-displacement device can be employed to sufficiently limit displacement of a prosthetic bone joint.

Figure 5:
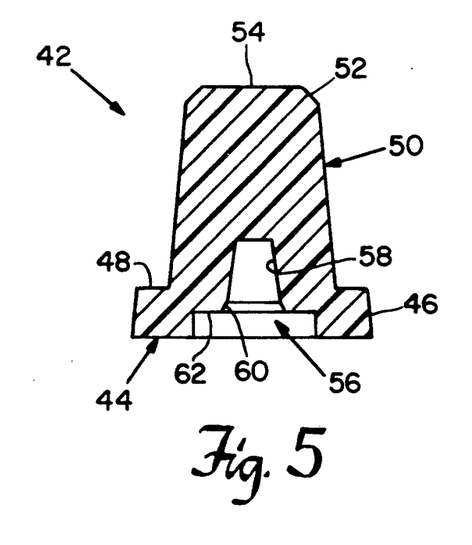
FIG. 5 is a section view of another embodiment of the present invention, wherein the biodegradable biocompatible anti-displacement device comprises a peg having a head, a shank extending from the head and a socket for receiving an insert tool for implanting the peg in a prosthetic bone joint.

In one embodiment, the biodegradable biocompatible anti-displacement device comprises peg 42, shown in FIG. 5. Peg 42 includes head 44 which is dimensioned and configured to form an interference fit with a cup, not shown, of a prosthetic bone joint, also not shown. Head 44 can be tapered at face 46. In one embodiment, head 44 has an inward taper at face 46 which extends from a major axis of peg 42 at an angle which is less than about 5°30'. Alternatively, head 44 can be cylindrically shaped. Annular ring 48 extends between face 46 and shank 50. In a preferred embodiment, head 44 has a diameter in the range of between about twelve millimeters and about fifteen millimeters.

Shank 50 extends from head 44 and can include chamfer 52 at a shank end 54 which is distally located from head 44. Shank 50 can be inwardly tapered for providing a suitable interference fit with bone tissue, not shown. In one embodiment, shank 50 is inwardly tapered from a major axis of peg 44 at an angle in the range of between about 4°30' and about 5°30'. In a preferred embodiment, shank 50 has a diameter in the range of between about five millimeters and about ten millimeters where shank 50 meets head 44, and a length in the range of between about ten millimeters and about forty millimeters.

In one embodiment, peg 42 defines a receiving portion 56 of peg 42 which includes socket 58, chamfer 60 and counterbore 62. Socket 58 is dimensioned and configured for receiving an insert tool, not shown, to support peg 42. An interference fit can be formed between socket 58 and the insert tool to secure peg 42 to the insert tool during implantation of peg 42 into the prosthetic bone joint and the bone. Chamfer 60 and counterbore 42 can operate by guiding the insert tool toward socket 58 during placement of peg 42 onto the insert tool.

In a method of implanting a prosthetic bone joint in a bone, the bone is suitably cut to expose suitable bone tissue for fixation of the prosthetic bone joint. A suitable cup of the prosthetic bone joint is placed in the bone at the exposed bone tissue. In one embodiment, the bone is a human acetabulum 64, shown in FIG. 6. Suitably cutting cortical bone tissue 65 of acetabulum 64 exposes bone tissue 66 of acetabulum 64 and forms recessed portion 68. An example of a suitable cup for placement in recessed portion 68 is acetabular cup 70.

Figure 6:
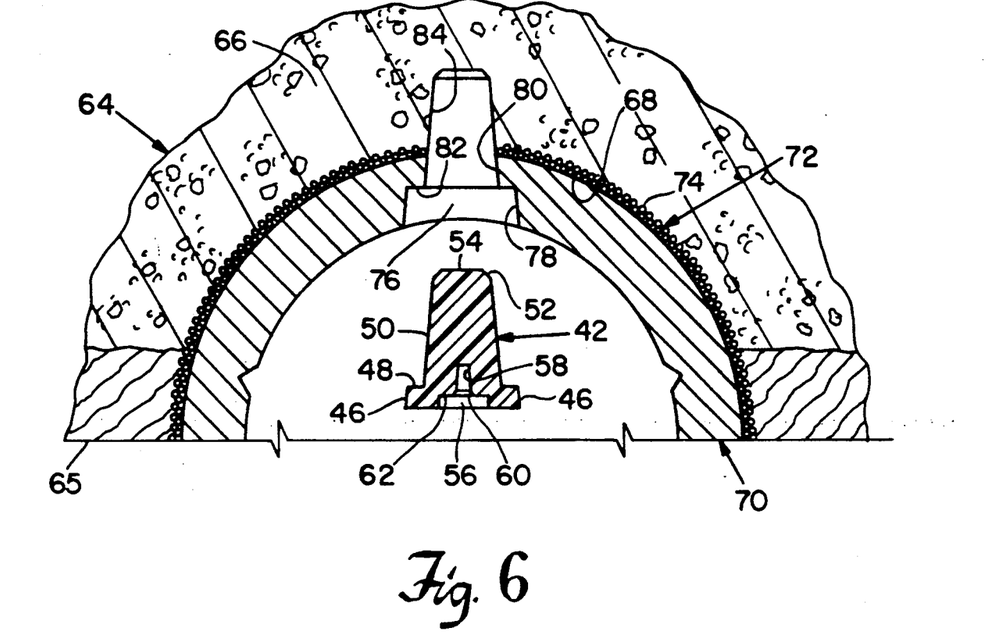
FIG. 6 is a section view of a portion of a human acetabulum and of an acetabular cup of a prosthetic bone joint which has been implanted in the acetabulum. The acetabular cup defines an orifice which is coaxially aligned with a bore which has been formed in the acetabulum for implantation of the embodiment of the biodegradable biocompatible anti-displacement device of the present invention illustrated in FIG. 5. A section view of the embodiment of the biodegradable biocompatible anti-displacement device of the present invention illustrated in FIG. 5 is also shown wherein the biodegradable biocompatible anti-displacement device is aligned with the orifice and bore for implantation into the acetabulum.

Acetabular cup 70 is fabricated of a suitable material for implantation in bone tissue 66. Examples of suitable materials include cobalt/chromium alloy and titanium. Surface portion 72 of acetabular cup 70 is suitable for allowing bone tissue growth at surface portion 72 to thereby fix acetabular cup 70 to bone tissue 66 of acetabulum 64.

An example of a suitable surface portion 72 comprises cobalt/chromium beads 74 fixed to acetabular cup 70.

Beads 74 can have a diameter in the range of between about 0.5 millimeters and about 0.75 millimeters. The depth of beads 74 at acetabular cup 70 can be in the range of about one millimeter and about 1.5 millimeters. The beads 74 form pores having an average diameter in the range of between about 280 microns and about 300 microns.

Acetabular cup 70 defines orifice 76. Acetabular cup 70 includes an outward cylindrical wall 78 at orifice 76 for providing an interference fit with face 46 of peg 42. Acetabular cup 70 can also include inward cylindrical wall 80 at orifice 76. Step 82 can extend between outward cylindrical wall 78 and inward cylindrical wall 80. Inward cylindrical wall 80 can be dimensioned for providing an interference fit with shank 50 of peg 42. Bore 84 of suitable diameter and length is formed in bone tissue 66 at orifice 76 of acetabular cup 70. Bore 84 is dimensioned to form an interference fit between bone tissue 66 and shank 50 of peg 42.

Figure 7:
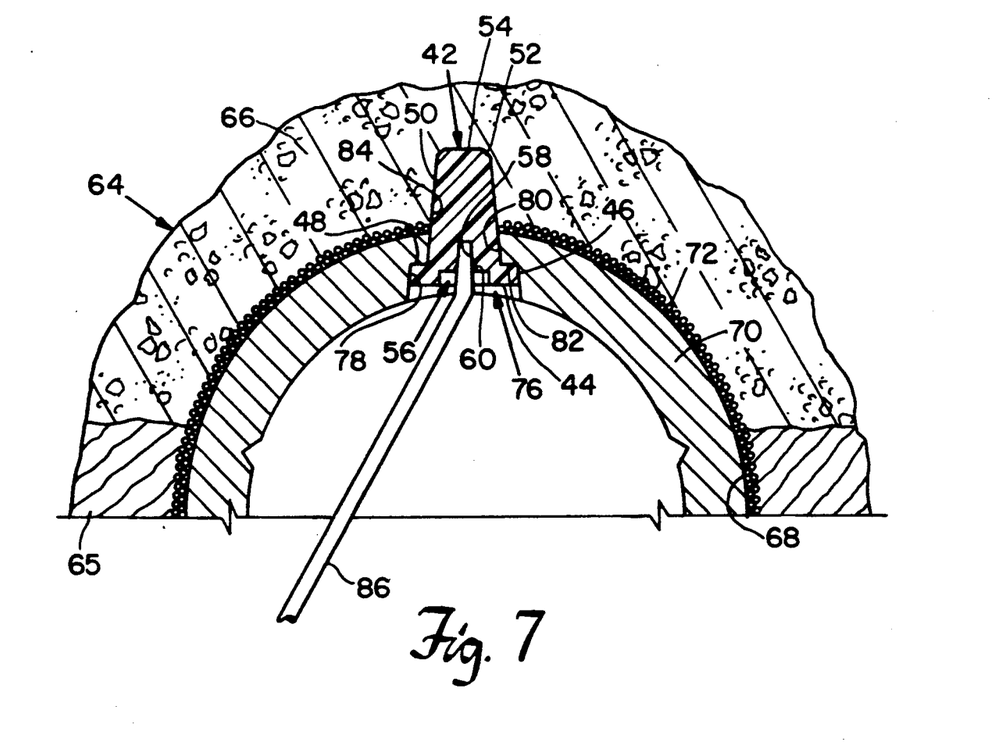
FIG. 7 is a section view of the acetabulum, the acetabular cup and the biodegradable biocompatible anti-displacement device illustrated in FIGS. 5 and 6 and of an insert tool disposed within the socket of the biodegradable biocompatible anti-displacement device, wherein the biodegradable biocompatible anti displacement device has been directed through the orifice and into the bore by the insert tool, the biodegradable biocompatible anti-displacement device thereby being implanted in the acetabulum.

As can be seen in FIG. 7, peg 42 is implanted in acetabulum 64 by fitting peg 42 onto insert tool 86 at socket 58. Peg 42 can then be manually directed by insert tool 86 through orifice 76 into bore 84 within bone tissue 66. Continued delivery of peg 42 through orifice 76 causes interfering contact between peg 42 and bone tissue 66 at bore 84. An interference fit is thereby formed between shank 50 and bore 84.

Peg 42 and orifice 76 are dimensioned to limit displacement between peg 42 and acetabular cup 70 to less than about one hundred and fifty microns over a period of twelve weeks when peg 42 and acetabular cup 70 are implanted in acetabulum 64. In a preferred embodiment, an interference fit is formed between shank 50 and inward cylindrical wall 80 of acetabular cup 70. An interference fit can also be formed between face 46 and outward cylindrical wall 78 of acetabular cup 70. Peg 42 can be directed into bore 84 until annular ring 48 abuts step 82. Displacement of acetabular cup 70 within recessed portion 68 of bone tissue 66 is thereby sufficiently limited by peg 42 to allow bone tissue growth at surface portion 72 of acetabular cup 70 to fix acetabular cup 70 to bone 64.

Figure 8:
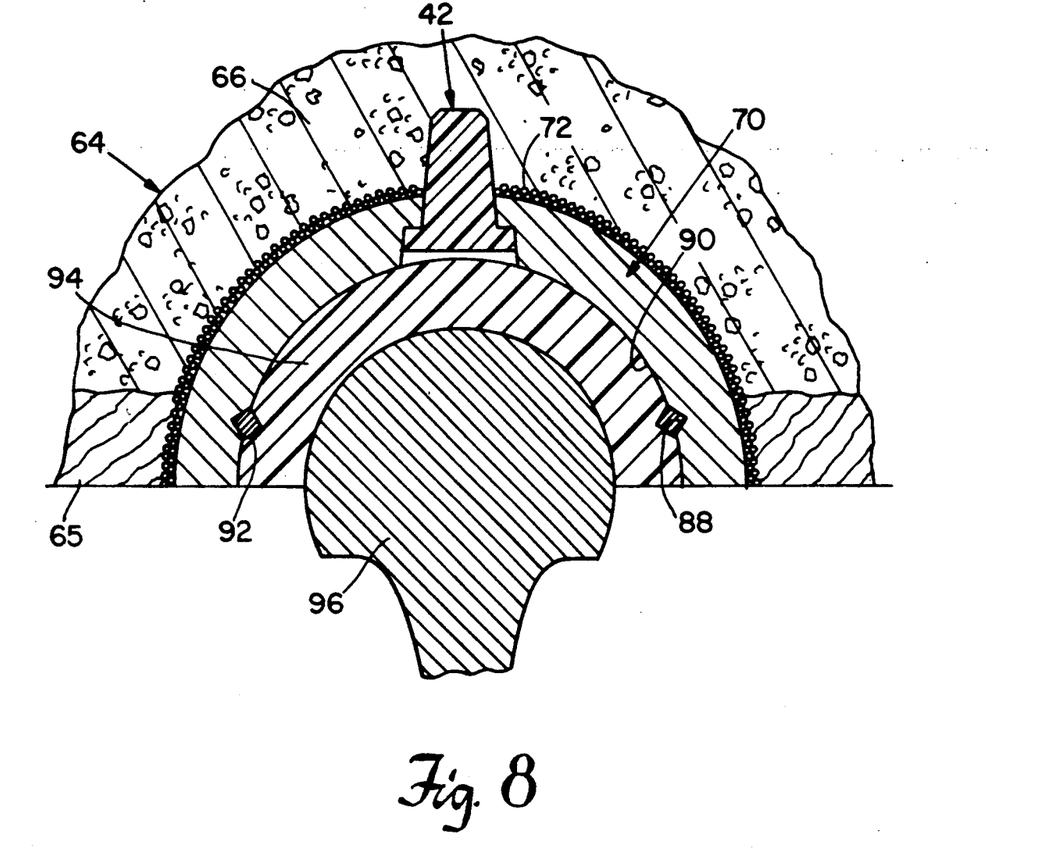
FIG. 8 is a section view of the acetabulum, the acetabulur cup, the biodegradable biocompatible anti-displacement device illustrated in FIGS. 5, 6 and 7 and of a liner and a femoral head of the prosthetic bone joint which have been assembled into the acetabular cup following removal of the insert tool from the socket of the biodegradable biocompatible anti displacement device.

As can be seen in FIG. 8, groove 88, defined by interior portion 90 of acetabular cup 70, receives locking ring 92 for securing prosthetic liner 94 within acetabular cup 70. Interior portion 90 of acetabular cup 70 receives prosthetic liner 94. Prosthetic liner 94 is formed of a suitable material, such as polyethylene. Locking ring 92 can be formed of a suitable material. An example of a suitable material is a cobalt/chromium alloy. Locking ring 92 provides an interference fit between acetabular cup 70 and prosthetic liner 94, thereby securing prosthetic liner 94 within acetabular cup 70. Prosthetic liner 94 receives prosthetic femoral head 96.

Following implantation of acetabular cup 70 and peg 42, displacement of acetabular cup 70 is sufficiently limited by peg 42 to allow bone tissue growth to interpenetrate surface portion 72 and permanently fix acetabular cup 70 to bone tissue 66 of acetabulum 64. Body fluids contact peg 42 to cause biodegradation of peg 42. In a preferred embodiment, peg 42 comprises suitable poly(L(−)lactide). Water contained in body fluid, such as blood which circulates through bone tissue 66, contacts peg 42 and causes hydrolysis of the poly(L(−)lactide). Peg 42 is thereby innocuously degraded and dissipated by the body fluid.

The biodegradable biocompatible anti-displacement device of the present invention can also be employed for implantation of other types of prosthetic joints. Examples of other suitable prosthetic bone joints for use with the present invention include prosthetic human and other mammalian elbows, shoulders, ankles, knees and other joints where prostheses can be fixed by growth of bone tissue.

Those skilled in the art will be able to ascertain, using no more than routine experimentation, many equivalents to the suitable biodegradable biocompatible polymers described specifically herein Additional examples of suitable biodegradable biocompatible polymers include biodegradable aliphatic polymers such as polycitric acid, polymalic acid, polyanhydrides and polyesters derived from hydroxycarboxylic acids which degrade by hydrolysis during exposure to water under suitable conditions. Examples of polyesters of hydroxycarboxylic acid include polymers and copolymers of glycolides and both racemic and optically active forms of lactides. Examples of biodegradable polymers and copolymers of lactides and glycolides include polyglycolides and racemic and optically active forms of polylactides and copoly(lactic/glycolic) acid.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A device for sufficiently limiting displacement of a cup of an implanted prosthetic bone joint to allow bone tissue growth at the cup to fix said prosthetic bone joint to the bone, comprising: an elongate member, at least a portion of which is formed of a biodegradable biocompatible polymer, said portion of the elongate member extending through said cup and in interfering contact with said cup, and into interfering contact with bone tissue, whereby displacement of the cup of the prosthetic bone joint is sufficiently limited to allow bone tissue growth at the cup to fix said prosthetic bone joint to the bone, and whereby the elongate member is thereafter biodegraded by body fluid at the bone tissue contacting the elongate member.

2. A device of claim 1 wherein the elongate member has a shear resistance of greater than about fifteen mpa during exposure to bone tissue over a period of time greater than about twelve weeks.

3. A device of claim 2 wherein the elongate member limits displacement to less than about one hundred and fifty microns over a period of time greater than about twelve weeks.

4. A device of claim 3 wherein the elongate member comprises a spike.

5. A device of claim 3 wherein the elongate member comprises a screw.

6. A device of claim 3 wherein the elongate member comprises a peg.

7. A device of claim 6 wherein the peg includes a head for providing an interference fit of the peg with the cup.

8. A device of claim 7 wherein the peg further includes a shank extending from the head for providing an interference fit of the peg with the bone tissue.

9. A device of claim 8 wherein the shank further provides an interference fit of the peg with the cup.

10. A device of claim 9 wherein the peg defines a receiving portion for receiving an insert tool.

11. A device of claim 10 wherein the shank includes a chamfered portion and a shank end located distally from said head.

12. A device of claim 11 wherein the peg comprises a biodegradable biocompatible polymer of lactide.

13. A device of claim 12 wherein the polylactide comprises poly(L(—)lactide).

14. A device of claim 11 wherein the peg comprises a biodegradable biocompatible polymer of anhydride.

15. A device of claim 11 wherein the peg comprises a biodegradable biocompatible polymer of glycolide.

16. In a method for fixing a prosthetic bone joint to a bone:

the improvement comprising directing an elongate member, at least a portion of which is formed of a biodegradable biocompatible polymer, through an orifice defined by a cup of the prosthetic bone joint, said portion forming an interfering contact with said cup and with bone tissue of the bone, whereby displacement of said cup is sufficiently limited by the elongate member to allow bone tissue growth at the cup to fix the prosthetic bone joint to the bone and whereby the elongate member is biodegrated by body fluid at the bone tissue contacting the elongate member.

* * * * *